United States Patent [19]

Tanaka et al.

[11] Patent Number: 4,902,837
[45] Date of Patent: Feb. 20, 1990

[54] PROCESS FOR PREPARING BIPHENOLS

[75] Inventors: Michio Tanaka; Yoshito Kurano; Katsuo Taniguchi, all of Iwakuni, Japan

[73] Assignee: Mitsui Petrochemical Industries, Ltd., Tokyo, Japan

[21] Appl. No.: 219,151

[22] PCT Filed: Oct. 14, 1987

[86] PCT No.: PCT/JP87/00770
§ 371 Date: Jun. 13, 1988
§ 102(e) Date: Jun. 13, 1988

[87] PCT Pub. No.: WO88/02745
PCT Pub. Date: Apr. 21, 1988

[30] Foreign Application Priority Data

Oct. 14, 1986 [JP] Japan .................... 61-243381

[51] Int. Cl.$^4$ .................... C07C 37/11; C07C 39/14
[52] U.S. Cl. .................... 568/730; 568/722; 568/723
[58] Field of Search .................... 568/730, 722, 723

[56] References Cited

U.S. PATENT DOCUMENTS

| 3,306,875 | 2/1967 | Hay | 568/730 |
| 4,098,830 | 7/1978 | Rutledge | 568/730 |
| 4,410,736 | 10/1983 | Strom | 568/730 |
| 4,438,284 | 3/1984 | Strom | 568/730 |
| 4,447,656 | 5/1984 | Kershner | 568/730 |
| 4,482,754 | 11/1984 | Strom | 568/730 |

FOREIGN PATENT DOCUMENTS

| 11296 | 5/1980 | European Pat. Off. | 568/730 |
| 2745 | 4/1988 | World Int. Prop. O. | 568/730 |

Primary Examiner—Werren B. Lone
Attorney, Agent, or Firm—Sherman and Shalloway

[57] ABSTRACT

Processes for preparing biphenols by oxidation coupling of phenols, to which the present invention is directed, are characterized in that said oxidation coupling reaction is carried out under such conditions that the same diphenoquinones as those produced as by-products at the time when said oxidation coupling is effected are added to the reaction system. According to a preferred embodiment of the invention, moreover, the yield of biphenols can be enhanced by the reuse in the abovementioned reaction of diphenoquinones recovered from the reaction mixture containing the same.

12 Claims, 1 Drawing Sheet

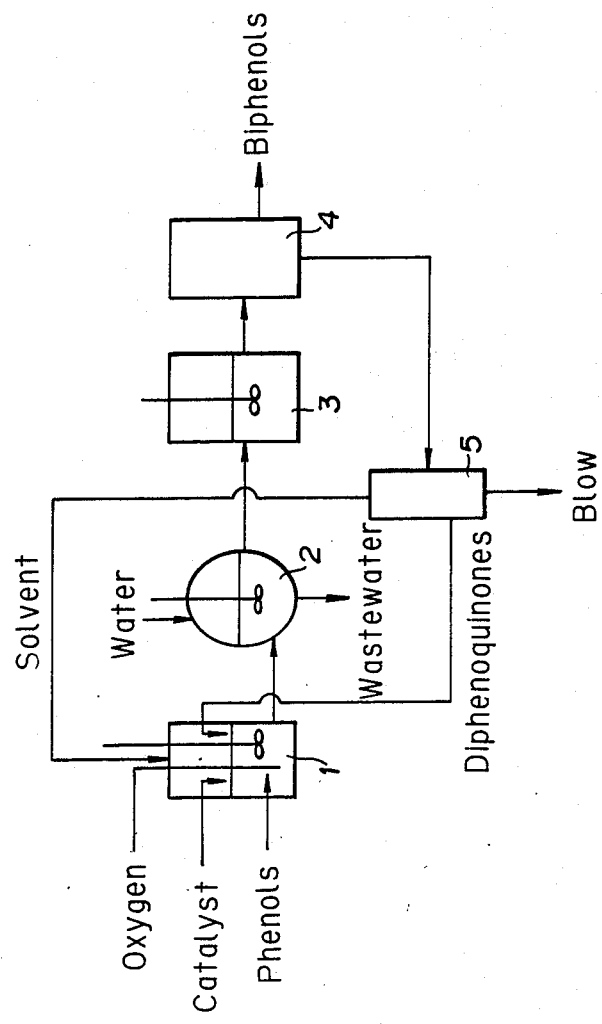

PROCESS FOR PREPARING BIPHENOLS

FIELD OF THE INVENTION

This invention relates to processes for preparing biphenols by oxidation coupling reaction of phenols.

BACKGROUND OF THE INVENTION

It is known that when phenols, particularly alkyl-substituted phenols are oxidized under specific conditions, oxidation coupling reaction is brought about to form biphenols and diphenoquinones as reaction products. Of these products, biphenols recovered are used as antioxidants, modifiers for synthetic resins such as polyesters or polycarbonates, dyes, intermediates of pharmaceutical preparations or agricultural chemicals, or photographic chemicals.

In this connection, the oxidation coupling reaction of phenols, particularly alkyl-substituted phenols, when carried out according to the conventionally known methods, for example, such processes as taught by U.S. Pat. Nos. 3,306,874, or 3,306,875, scarcely forms the desired product biphenols, whereby mainly formed are diphenoquinones which are the oxidation products of biphenols which have been further oxidized. On that account, it was necessary to convert again the diphenoquinones formed by the above-mentioned reaction into biphenols by some measures, for example, reduction of said diphenoquinones with hydrogen in order to obtain the desired product biphenols. According to the processes disclosed in the above-mentioned U.S. Patents' specifications, there was such a problem that in addition to the diphenoquinones, biphenyl ethers, polyphenylene ethers, etc. are formed thereby. Just for information, an equation is given below to illustrate oxidation coupling reaction of 2,6-disubstituted phenol.

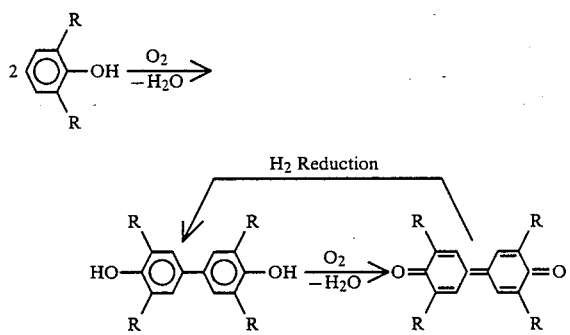

With the purpose of solving such problems referred to above, there have been proposed various processes for preparing alkyl-substituted biphenols in enhanced selectivity by controlling formation of diphenoquinones when alkyl-substituted phenols are oxidized. For example, Japanese Patent Laid-Open-to-Public Publn. No. 72131/1980 discloses a process for preparing alkyl-substituted biphenols by oxidation of alkyl-substituted phenols in the presence of alkaline catalysts, such as alkali metal hydroxides, weak acid alkali metal salts, alkaline earth metal hydroxides and weak acid alkaline earth metal salts, while strictly controlling the amount of oxygen present in the reaction system.

In the above-mentioned process, however, there is involved such a problem that because it is very difficult to control the oxygen amount so as to form no diphenoquinones, the formation of the diphenoquinones is unavoidable.

Further, Japanese Patent Publication No. 15293/1971 discloses a process for preparing alkyl-substituted biphenols, characterized by oxidizing alkyl-substituted phenols with oxygen in the presence of alkali metal hydroxides up to diphenoquinones, and incorporating the resulting reaction mixture with alkyl-substituted phenols, thereby effecting reaction between the diphenoquinones and alkyl-substituted phenols in a nitrogen atmosphere.

In this process, however, there were involved such problems that a slow rate of reaction between the diphenoquinones and alkyl-substituted phenols requires a long period of time to complete the reaction, the efficiency of the formation of desired alkyl-substituted biphenols is poor and, moreover, said process is scarcely fit for the continuous process for the preparation of the alkyl-substituted biphenols.

Still further, Japanese Patent Laid-Open-to-Public Publn. No. 140034/1983 discloses a process for preparing alkyl-substituted biphenols, characterized by oxidizing alkyl-substituted phenols in the presence of alkali catalysts to form a reaction mixture comprising alkyl-substituted biphenols and diphenoquinones, and incorporating the reaction mixture with water-immiscible organic solvents to form a two-layer system, followed by hydrogenation in the presence of hydrogenation catalysts.

In this process, however, there were involved such problems that there is a risk of explosion because of the step of reduction with hydrogen involved in this process and, moreover, a life of the hydrogenation catalyst used is short because the alkali catalyst used in the oxidation reaction acts as a catalyst poison.

The present invention is intended to solve such problems associated with the prior art as mentioned above, and its object is to provide a process for obtaining biphenols particularly dialkyl-substituted biphenols in high yields from phenols particularly alkyl-substituted phenols.

DISCLOSURE OF THE INVENTION

The process for preparing biphenols of the present invention is characterized in that when the biphenols are intended to be prepared by oxidation coupling of phenols, said reaction is carried out under the conditions such that the same diphenoquinones as those formed in said oxidation coupling as by-products are added to the reaction system. According to preferred embodiments of the present invention, furthermore, the yield of desired biphenols can be improved by reusing in the above-mentioned reaction the diphenoquinones recovered from the above-mentioned reaction mixture.

BRIEF DESCRIPTION OF THE DRAWING

FIG. 1 is a flow sheet showing the process for preparing biphenols of the present invention.

| | |
|---|---|
| 1 ... Reaction vessel | 2 ... Oil water separator |
| 3 ... Crystallizer | 4 ... Centrifugal separator |
| 5 ... Distillation column | |

BEST MODE FOR PRACTICE OF THE INVENTION

The process for preparing biphenols of the present invention, including examples thereof, are illustrated below in detail.

In the present invention, phenols which are used as starting materials are represented by the following general formula [I], and of these phenols preferred are 2,6-dialkyl-substituted phenols.

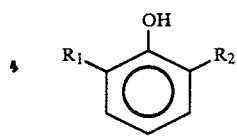

wherein $R_1$ and $R_2$ may be the same or different and each represent a hydrocarbon radical or alkoxy group having 1 to 8 carbon atoms.

Phenols represented by the above-mentioned general formula [I] include concretely, 2,6-dimethylphenol, 2,6-diisopropylphenol, 2,6-di-t-butylphenol, 2-ethyl-6-methylphenol, 2-isopropyl-6-methylphenol, 2-methoxy-6-methylphenol, 2-ethoxy-6-ethylphenol, 2,6-diphenylphenol, 2,6-dibenzylphenol, 2,6-dicyclohexylphenol, 2-isopropyl-6-methylphenol, etc.

Of these phenols exemplified above, particularly preferred are 2,6-xylenol, 2,6-di-t-butylphenol, 2,6-dicyclohexylphenol, 2,6-diisopropylphenol, etc.

The step of obtaining a reaction mixture comprising biphenols and diphenoquinones by oxidation coupling reaction of such phenols as mentioned above is known, per se. Given below is a reaction formula of the oxidation coupling reaction effected in that case.

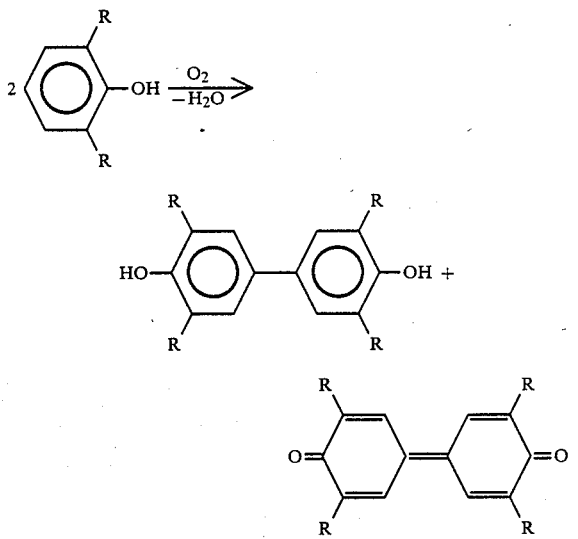

In the present invention, the above-mentioned reaction is carried out in the reaction system to which the same diphenoquines as those which have been produced as by products have been added. In that case, it is considered that phenols are oxidized in a liquid phase with molecular oxygen to form biphenols and diphenoquinones as shown in the above formula and, on one hand, the diphenoquinone thus formed react with the phenols in a manner like oxidation reduction to yield biphenols. It is possible, therefore, to control the reaction system so that diphenoquinones are not practically accumulated within said system. That is, it is considered that in the process for preparing biphenols of the present invention, the oxidation-reduction reaction of diphenoquinones with phenols is effected simultaneously with the oxidation coupling reaction of phenols. The oxidation-reduction reaction effect in that case is illustrated by way of the following formula.

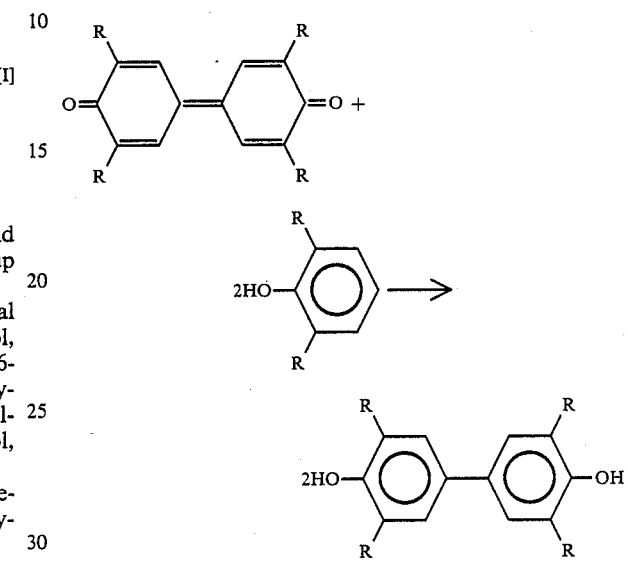

The reaction through which diphenoquinones are allowed to react with phenols to afford biphenols has heretofore been known. All the reactions of the type are carried out substantially in the absence of oxygen, as disclosed in the aforementioned Japanese Patent Publication No. 25077/1969 or 15293/1971. In the present invention, however, when biphenols are prepared by oxidation coupling reaction of phenols, said reaction is carried out by the addition to the reaction system of the same diphenoquinones as those produced as by-products when said oxidation coupling reaction is effected. In that case, the reaction is carried out in the presence of sufficient amounts of oxygen, and it is considered that the diphenoquinones react with phenols in a manner like oxidation-reduction simultaneously with the oxidation coupling reaction of phenols, whereby biphenols are formed from the reaction of the diphenoquinones with phenols. Such a process for preparing biphenols in accordance with the present invention has not been reported yet. It is a real surprise to find such a novel knowledge that even in the presence of sufficient amounts of oxygen where oxidation coupling reaction can take place, biphenols can be prepared efficiently in high yields by adopting the process of the present invention which comprises carrying out the oxidation coupling reaction of phenols by the addition to the reaction system of the by-product diphenoquinones. This novel knowledge found out by the present inventors is one of the factors by which the present invention is accomplished.

In the present invention, usually the reaction is carried out preferably by the use of catalysts therefor, though the reaction proceeds even in the absence of catalysts. Preferred catalysts used in the reaction are alkali catalysts. Useful alkali catalysts include alkali metal hydroxides, alkaline earth metal hydroxides, weakly acidic alkali metal salts and weakly acidic alkaline earth metal salts such as sodium hydroxide, potassium hydroxide, calcium carbonate, potassium carbonate, calcium hydroxide, calcium carbonate, etc.

In the practice of the above-mentioned reaction, there can also be used as a catalyst at least one salt of metal selected from the group consisting of manganese, iron, copper, cerium, vanadium, molybdenum and palladium.

The metal salts referred to above include halides, basic halohydroxides, carboxylates, hydrochlorides, nitrates, sulfates, carbonates, hydroxides, chlorates and acetylacetone salts of the above-mentioned metals.

Concretely exemplified as the halides are manganese chloride, iron chloride, cerium chloride, vanadyl chloride, molybdenum chloride, palladium chloride, copper chloride, manganese bromide, iron bromide, copper bromide, copper iodide, etc.

Concretely exemplified as the carboxylates are manganese acetate, iron acetate, copper acetate, molybdenum acetate, cerium acetate, palladium acetate, iron benzoate, copper benzoate, vanadyl oxalate, manganese oxalate, etc.

Concretely exemplified as the nitrates are manganese nitrate, cerium nitrate, palladium nitrate, copper nitrate, etc., and as the sulfates are manganese sulfate, iron sulfate, vanadyl sulfate, palladium sulfate, copper sulfate, etc.

Furthermore, the basic carbonates include $CuCO_3$—$Cu(OH)$, etc., the chlorates include $Cu(ClO_3)_2$, etc., and the acetylacetone salts include manganese acetylacetonate, iron acetylacetonate, vanadium acetylacetonate, molybdenum acetylacetonate, molybdenum oxide acetylacetonate, etc. These compounds exemplified above are desirably used in their dry state, however, even those having water of crystallization or having absorbed moisture can be used sufficiently. Furthermore, the above-exemplified compounds can also be used in combination of a plurality of species.

Usually, such catalysts as mentioned above are preferably used in an amount of 0.005-1 mole based on 1 mole of the starting phenols.

As mentioned previously, the reaction of the present invention may be carried out either in the absence or presence of solvent. Preferably usable solvents in the latter case are hydrocarbons of 6-15 carbon atoms, preferably 8-15 carbon atoms, including concretely benzene, toluene, p-xylene, m-xylene, mixed xylene, pseudocumene, durene, cumene, diisopropylbenzene, triisopropylbenzene, etc. Of these solvents, particularly preferred is p-xylene.

Furthermore, compounds having in the molecule an amide bond can also be used in the reaction of the present invention as the solvents mentioned above. Typical examples of such compounds include those as enumerated below.

N,N-dimethylformamide, N,N-diethylformamide, N,N-dipropylformamide, N,N-dimethylacetamide, N,N-diethylacetamide, N,N-dimethylpropionamide, formpiperidine, formpyrolidine, acetylpiperidine, acetylprolidine, formanilide, N-methylacetanilide, acetylpyridine, N-methylformtoluide, acetoluide, dimethylbenzamide, tetramethylurea, N,N-dimethyltolylurea, succineimide, glutalimide, phthalimide, etc.

Of the compounds exemplified above, particularly preferred are N,N-dimethylformamide, N,N-diethylformamide, N,N-dimethylacetamide, tetramethylurea, etc.

Where the reaction is carried out in the presence of solvent, such solvents as exemplified above are used usually in an amount of 0.1-100 moles, preferably 5-50 moles based on 1 mole of the starting phenols.

In the process for preparing biphenols of the present invention, the reaction is carried out usually at a temperature of 70°-300° C., preferably 120°-250° C. The reaction time is usually about 0.2-5 hours, though it may be widely varied according to the reaction temperature employed.

The above-mentioned reaction is carried out in the presence of oxygen. Oxygen which is introduced into the reaction system includes pure oxygen or oxygen-containing gases prepared by diluting air or oxygen with inert gases such as nitrogen This reaction is carried out usually at normal pressures or under pressure. Where the reaction is carried out at normal pressures, pure oxygen or oxygen-containing gas is introduced into the reaction system by bubbling said pure oxygen or oxygen-containing gas through the reaction liquid and, on one hand, when the reaction is carried out under pressure, pure oxygen or oxygen containing gas can be introduced by injection or the like means into the reaction system. After the completion of the invention, the inside of the system can be flushed with an inert gas such as nitrogen.

In the present invention, the proportion of oxygen introduced into the reaction system is usually 0.001-1.5N $m^3$/hr, preferably 0.001-0.1N $m^3$/hr based on 1 mole of the starting phenols.

In carrying out the reaction of the present invention, the diphenoquinones which are the same as those formed as by products in the oxidation coupling of the starting phenols are added to the reaction system usually in a proportion of 0.1-40 moles, preferably 1-30 moles based on 100 moles of the starting phenols, though no particular limitation is placed thereon.

The synthesis reaction of biphenols in accordance with the present invention is preferably carried out by a continuous process, though it can be carried out either by a continuous process or batchwise operation.

In accordance with the synthesis reaction of biphenols of the present invention, there are formed in high selectivity biphenols [II] as represented by the following general formula [II].

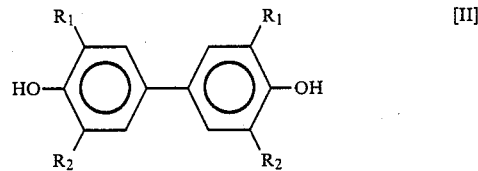

wherein $R_1$ and $R_2$ are individually as defined previously.

Such biphenols [II] as shown above include various compounds according to the starting phenols [I] used therefor. Examples of preferred compounds [II] are 3,3',5,5'-tetramethyl-4,4'-dihydroxydiphenyl, 3,3',5,5'-tetraisopropyl-4,4'-dihydroxyphenyl, 3,3',5,5'-tetra-t-butyl-4,4'-dihydroxyphenyl, etc.

In carrying out the process for preparing biphenols of the present invention, it is preferable to adopt embodiments as will be mentioned hereinafter. That is, in the present invention where the oxidation coupling of phenols to afford the desired biphenols, said reaction is effected by the addition thereto of the same diphenoquinones as those which are formed as by-products of said oxidation coupling. In that case, however, it is preferable to use diphenoquinones which have been recovered from the reaction mixture obtained in said oxidation coupling. Furthermore, the addition to the reaction system of the recovered diphenoquinones is preferably effected by using a diphenoquinone-containing crystallization mother liquor resulting from the removal operation of the desired biphenols by separation from the reaction mixture. This crystallization mother liquor, when it is used, is preferably a diphenoquinone-containing crystallization mother liquor which has been obtained by removal of separation of the desired biphenols from the reaction mixture containing the same obtained in the aforesaid oxidation coupling reaction containing aromatic hydrocarbon of 6-15 carbon atoms. In other words, the embodiment illustrated above is an exemplification of a preferred embodiment of the present invention wherein step (A), step (B) and step (C) are combined together in sequence. That is, it is preferable to employ an embodiment of the present invention for the preparation of biphenols by the addition to the reaction system, wherein the following steps are combined together in sequence;

(A) a step of effecting in a reaction section a reaction to afford biphenols by oxidizing phenols in a liquid phase with molecular oxygen, and also a reaction to afford biphenols by reacting diphenoquinones with phenols, thereby obtaining a reaction mixture containing biphenols and diphenoquinones, (B) a step of separating biphenols from the reaction mixture obtained above, and separating the reaction mixture into a deposit of biphenols and a crystallization solution containing diphenoquinone, and (C) a step of returning diphenoquinone present in the crystallization solution to the reaction section.

The reactions individually carried out in the above-mentioned reaction section are as mentioned previously, and a reaction mixture containing biphenols and diphenoquinones is obtained thereby.

After the completion of the reactions in the step (A), the reaction mixture is preferably washed with water, prior to effecting the subsequent step (B), to remove a catalyst such as potassium hydroxide.

Subsequently, the reaction mixture thus obtained is subjected to the step (B). In this step (B), biphenols are separated from the reaction mixture to obtain a deposit of biphenols and a crystallization solution containing diphenoquinones. A crystallization solvent used for separating biphenols from the reaction mixture are illustrated hereinafter.

Examples of the crystallization solvent used in that case are aromatic hydrocarbons of 6-15 carbon atoms such as benzene, toluene, p-xylene, mixed xylene, ethylbenzene, cumene, cymene, diisopropylbenzene, triisopropylbenzene, etc., aliphatic hydrocarbons of 6-15 carbon atoms such as decane, tridecane, pentadecane, hexane, octane, etc., and alicyclic hydrocarbons of 5-8 carbon atoms such as cyclopentane, cyclohexane, methylcyclohexane, dimethylcyclohexane, etc. Of these solvents exemplified above, aromatic hydrocarbons are preferable, and particularly preferred are p-xylene and cumene.

Where the same solvent as the crystallization solvent as used in the step (B) was used in the step (A) as a reaction solvent, the step (B) may be carried out, as it is, while using said reaction solvent as the crystallization solvent. However, when a reaction solvent was not used in the step (A) or when a reaction solvent was used in the step (A) but said reaction solvent was not the same as a crystallization solvent intended to use in the step (B), the above-exemplified crystallization solvent must be used afresh in the step (B) after removing, if necessary, said reaction solvent from the reaction mixture after the completion of the step (A).

Such crystallization solvents as mentioned above are preferably present in the reaction mixture in the step (B) in an amount of about 40-90% by weight based on the reaction mixture. The crystallization temperature employed is preferably from 0° C. to 100° C., though it may vary usually from 0° C. to a temperature at which the crystallization solvent refluxes.

In this connection, the aforementioned waterwashing to be effected, prior to carrying out the step (B), may also be practiced after the addition of a crystallization solvent to the reaction mixture obtained in the step (A).

When the reaction mixture thus obtained after incorporation thereinto of the crystallization solvent is cooled to about room temperature, biphenols separate from the reaction mixture and, on one hand, diphenoquinones remain dissolved, as they are, in the reaction mixture, whereby the biphenols as deposited can readily be separated by such operation as centrifugal separation from the crystallization mother liquor containing diphenoquinones. The reason why such separation can be performed is that biphenols do not practically dissolve in the crystallization solvent used and, on one hand, diphenoquinones sufficiently dissolve in said crystallization solvent.

The biphenols thus separated can be purified, for example, by washing them with the crystallization solvent. In that case, the washing solution used can also be reused by the addition thereof to the crystallization mother liquor used in the subsequent step (C) as will be mentioned later.

After the separation of biphenols in the step (B) from the reaction mixture, the crystallization mother liquor containing diphenoquinones thus obtained may be sent back, as it is, to the reaction section of the step (A) through the step (C).

In either case, the whole or part of the diphenoquinones present in the crystallization mother liquor is subjected to blow treatment and then sent back to the reaction section.

The diphenoquinones sent back to the reaction section react with the starting phenols to yield biphenols, as stated previously.

In the present invention, molecular oxygen is present in the reaction system. As mentioned previously, however, the present inventors found that even when molecular oxygen is present in the reaction section, biphenols are formed by the above-mentioned reaction which proceeds without being adversely affected by the presence of molecular oxygen, and thus the reaction can be carried out by controlling it so as not to accumulate diphenoquinones in the reaction system. On the basis of the above finding, the present inventors have eventually conceived the process for preparing biphenols according to the present invention.

A preferred embodiment of the process for preparing biphenols of the present invention is illustrated below with reference to the accompanying flow sheet. Reactor 1 which constitutes the reaction section is charged with the starting phenols, a catalyst and, if necessary, a solvent, and molecular oxygen such as air is blown into said reactor 1. After the completion of the reaction, if necessary, the reaction mixture is transferred to oil water separation tank 2 wherein the reaction mixture is washed with water and separated into an oil phase and an aqueous phase, the aqueous phase is discarded and, on one hand, the oil phase is introduced into crystallizer 3.

In the crystallizer 3, the reaction mixture is cooled in a state where an aromatic hydrocarbon of 6–15 carbon atoms is present in said reaction mixture to about room temperature, whereupon biphenols begin to separate from the reaction mixture. Therefore, this reaction mixture is fed to centrifugal separator 4, wherein the separated biphenols are separated therefrom. On one hand, the crystallization mother liquor containing diphenoquinones are sent back, either as it is or in a state where at least a part of the solvent has been removed and concentrated by distillation column 5, to reactor 1. In that case, the whole of the solvent is removed from the crystallization mother liquor to obtain diphenoquinones in a solid form and the solid diphenoquinones thus obtained may be sent back to reactor 1. Furthermore, the crystallization mother liquor, the crystallization mother liquor which has been concentrated, or the solid diphenoquinones which have been partly blown may be sent back to reactor 1, as well.

EFFECT OF THE INVENTION

According to the process for preparing biphenols of the present invention, diphenoquinones which are produced as by-products during oxidation coupling of phenols to yield biphenols can be converted to biphenols which are the end products of the present invention. Therefore, in comparison with the prior art processes, the present invention makes it possible to prepare biphenols from phenols in high purity as well as in high yields.

Furthermore, in an embodiment of the reaction of the process for preparing biphenols, wherein diphenoquinones produced as by-products during oxidation coupling of phenols to afford biphenols are sent back to the reaction section, particularly when the step (B) is carried out in the presence of aromatic hydrocarbon of 6–15 carbon atoms, diphenoquinones can selectively be separated from the reaction mixture containing the same and, at the same time, the separated diphenoquinones are sent back to the reaction section and allowed to react with the starting phenols to yield the desired biphenols. In accordance with the present invention, therefore, there are obtained such extremely excellent effects that not only the step of reducing diphenoquinones with hydrogen as required hitherto in the prior processes can be omitted but also high purity biphenols can be prepared in high yields from phenols by a continuous process.

The present invention illustrated below with reference to examples, but it should be construed that the invention is in no way limited to those examples.

EXAMPLE 1

Into a 500 ml autoclave equipped with an induction stirring device were charged 200 g of 2,6-di-t-butylphenol and 1 g of a 50% aqueous potassium hydroxide solution. The reaction was carried out for 0.5 hour at 200° C., while applying a pressure of up to 7 kg/cm$^2$ with oxygen to the reaction apparatus, whereupon 147.5 g of 3,3',5,5'-tetra-t-butylbiphenol and 11.0 g of 3,3',5,5'-tetra-t-butyldiphenoquinone were formed in the reaction mixture, leaving 31.7 g of unaltered 2,6-di-t-butylphenol.

The reaction mixture thus obtained was charged with 660 g of p-xylene, washed twice with water at 60° C., than transferred to a crystallizer and cooled to room temperature, whereupon crystals began to separate. The crystals were centrifuged, washed with 150 g of hexane and then dried, whereby 112.2 g of 3,3',5,5'-tetra-t-butylbiphenol of 99.8% purity was obtained.

One one hand, after mixing the crystallization mother liquor with the washing liquid, the solvent was removed from the mixture to obtain 79.2 g of a concentrated mother liquor. In this concentrated mother liquor, there was present 9.8 g of 3,3',5,5'-tetra-t-butyldiphenoquinone. Subsequently, 75 g of the concentrated mother liquor containing said diphenoquinone thus obtained and 125 g of 2,6-di-t-butylphenol were charged into the same autoclave as used above, and the reaction was carried out for 0.5 hour, while applying a pressure of 7 kg/cm$^2$G with oxygen, whereupon 148.1 g of 3,3',5,5'-tetra-t-butylbiphenol and 11.6 g of 3,3',5,5'-tetra-t-butyldiphenoquinone, leaving 19.4 g of unaltered 2,6-di-t-butylphenol.

The reaction mixture was subjected to separation, washing and drying in the same manner as above, whereby 112 g of 3,3',5,5'-tetra-t-butylbiphenol of 98.7% purity and 82.5 g of a concentrated mother liquor were obtained.

EXAMPLE 2

The crystallization mother liquor obtained in Example 1 was combined with the washing liquid obtained in Example 1 at the time when the 3,3',5,5'-tetra-t-butylbiphenol obtained was washed with p-xylene, and the mixture obtained was concentrated by distillation by means of the distillation column, whereby 75.3 g of dry solids were obtained. The dry solids thus obtained consisted essentially of 3,3',5,5'-tetra-t-butyldiphenoquinone.

The same reaction and subsequent treatments as in Example 1 were carried out except that 72 g of the dry solids obtained above were charged with 128 g 2,6-di-t-butylphenol, and the resulting mixture was used as the starting material and the reaction temperature was changed to 180° C. As the result, there was obtained 107.8 g of 3,3',5,5'-tetra-t-butyldiphenol of 98.1% purity. The 3,3',5,5'-tetra-t-butyldiphenoquinone content in the 3,3',5,5'-tetra-t-butylbiphenol thus obtained was less than 0.1%.

What is claimed is:

1. A process for preparing biphenols by oxidation coupling of phenols, characterized by carrying out said oxidation coupling reaction at a temperature of 70–300° C. in the presence of molecular oxygen under such conditions that the same diphenoquinones as the diphenoquinones produced as by-products at the time when said oxidation coupling is carried out are added to the reaction system.

2. The process as claimed in claim 1 wherein said phenols comprise 2,6-di-t-butylphenol.

3. The process as claimed in any of claims 1 and 2 wherein said diphenoquinones added to said reaction system are diphenoquinones which are recovered from said reaction.

4. The process as claimed in any of claims 1 or 2 wherein said addition to said reaction system of diphenoquinones is effected by the use of a crystallization mother liquor containing diphenoquinones obtained by separating and removing biphenols from said reaction system containing the same.

5. The process as claimed in claim 4 wherein said addition to said reaction system to diphenoquinones is effected by the use of a crystallization mother liquor containing diphenoquinones obtained by separating and removing biphenols from a crystallization mother liquor containing the same, to which an aromatic hydrocarbon of 6–15 carbon atoms has been added.

6. The process as claimed in claim 3 wherein said addition to said reaction system of diphenoquinones is effected by the use of a crystallization mother liquor containing diphenoquinones obtained by separating and removing biphenols from said reaction system containing the same.

7. The process as claimed in claim 6, wherein said addition to said reaction system of diphenoquinones is effected by the use of a crystallization mother liquor containing diphenoquinones obtained by separating and removing biphenols from crystallization mother liquor containing the same, to which an aromatic hydrocarbon of 6-carbon atoms has been added.

8. A process for preparing biphenols by oxidation coupling of phenols, said process comprising:

feeding a reaction mixture comprising a phenol of the formula

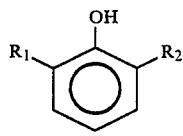

wherein
$R_1$ and $R_2$, which may be the same or different, each represent a hydrocarbon radical of 1 to 8 carbon atoms or an alkoxy group of 1 to 8 carbon atoms to an oxidation reactor;

oxidizing said reaction mixture to form a reaction product comprising a biphenol of the formula

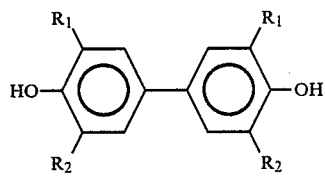

wherein
$R_1$ and $R_2$ are as defined above and a diphenoquinone of the formula

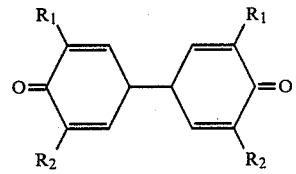

wherein
$R_1$ and $R_2$ are as defined above at a temperature of 70° to 300° C. in the presence of molecular oxygen in said oxidation reactor;

removing said reaction product from said oxidation reactor;

separating said reaction product into a first fraction comprising a major portion of said biphenol and a second fraction comprising a major portion of said diphenoquinone;

recycling at least a portion of said second fraction to said oxidation reactor.

9. The process of claim 8, wherein said oxidation is carried out in the presence of a catalyst.

10. The process of claim 8, wherein said oxidation is carried out in the presence of a solvent.

11. The process of claim 8, wherein said oxidation is carried out at a temperature of 120°–250° C.

12. The process of claim 8, wherein said separation of said reaction product into a first reaction comprising a major portion of said biphenol and a second fraction comprising a major portion of said diphenoquinone is effected by crystallization.

* * * * *